United States Patent [19]

Periana et al.

[11] Patent Number: 5,233,113
[45] Date of Patent: Aug. 3, 1993

[54] PROCESS FOR CONVERTING LOWER ALKANES TO ESTERS

[75] Inventors: Roy A. Periana, San Jose; Eric R. Evitt, Mountain View; Henry Taube, Stanford, all of Calif.

[73] Assignee: Catalytica, Inc., Mountain View, Calif.

[21] Appl. No.: 656,910

[22] Filed: Feb. 15, 1991

[51] Int. Cl.$^5$ .............................................. C07C 2/00
[52] U.S. Cl. ................................... 585/500; 585/469; 585/638; 585/733; 585/943; 560/302; 560/304; 560/305; 560/318
[58] Field of Search ............... 585/733, 638, 310, 314; 560/302, 304, 305, 318; 423/304, 573, 469, 500

[56] References Cited

U.S. PATENT DOCUMENTS

| | | | |
|---|---|---|---|
| 3,702,886 | 11/1972 | Argauer et al. | 423/328 |
| 3,894,107 | 7/1975 | Butter et al. | 260/688 |
| 3,928,483 | 12/1975 | Chang et al. | 260/668 R |
| 3,979,470 | 9/1976 | Firnhaber et al. | 260/658 R |
| 3,979,472 | 9/1976 | Butter et al. | 260/668 R |
| 4,373,109 | 2/1983 | Olah | 585/640 |
| 4,523,040 | 6/1985 | Olah | 568/671 |
| 4,524,234 | 6/1985 | Kaiser | 585/638 |
| 4,543,434 | 9/1985 | Chang | 585/310 |
| 4,579,996 | 4/1986 | Font Friede et al. | 585/642 |
| 4,621,161 | 11/1986 | Shihabi | 585/733 |
| 4,687,875 | 8/1987 | Currie et al. | 585/469 |
| 4,709,113 | 11/1987 | Harandi et al. | 585/733 |
| 4,804,797 | 2/1989 | Minet et al. | 585/500 |
| 4,822,938 | 4/1989 | Audeh et al. | 585/733 |
| 4,864,073 | 9/1989 | Han et al. | 585/943 |
| 4,864,074 | 9/1989 | Han et al. | 585/943 |

FOREIGN PATENT DOCUMENTS 1214644 2/1986 U.S.S.R. .

OTHER PUBLICATIONS

Olah et al Agew. Chem. Intl. Ed. Enge 17, 909–931, 1978.
Rudakav et al Russ J. Phys. Chem. 49, 1610–1611, 1975.
Tret'yakov et al Doklady Acad. SSSR, 245, 1135–1138 (Translation, Plenum Publishing Corp.
A. E. Shilov and A. A. Shteinman, "Activation of Saturated Hydrocarbons by Metal Complexes in Solutions", *Kinetka i Kataliz*, vol. 18, No. 5, pp. 1129–1145, 1977.
Sen et al., "Palladium (II) Mediated Oxidative Functionalization of Alkanes and Arenes", *New Journal of Chemistry* (1989), vol. 13, No. 10-11, pp. 756–760.
Vargaftik et al., "Highly Selective Partial Oxidation of Methane to Methyl Trifluoroacetate", *Journal of the Chemical Society, Chemical Communications* (1990), pp. 1049–1050.
Olah et al., "Superacid-Catalyzed Oxygenation of Alkanes", *Angew, Chem. Int. Ed.*, (1978) vol. 17, pp. 909–931.
Lien-Chung Kao, Alan C. Hutson, and Ayusman Sen, "Low-Temperature, Palladium (II)-Catalyzed, Solution-Phase Oxidation of Methane to a Methanol Derivative", J. Am. Chem. Soc. 1991, 113, 700–701.
Efi Gretz, Thomas F. Oliver, and Ayusman Sen, "Carbon-Hydrogen Bond Activation by Electrophilic Transition-Metal Compounds, Palladium (II)-Mediated Oxidation of Arenes and Alkanes Including Methane", J. Am. Chem. Soc. 1987, 109, 8109–8111.

(List continued on next page.)

Primary Examiner—Asok Pal
Assistant Examiner—P. Achutamurthy
Attorney, Agent, or Firm—Morrison & Foerster

[57] ABSTRACT

This invention is a process for converting lower alkanes into their corresponding esters and optionally into various intermediates (such as methanol) and other liquid hydrocarbons. The alkanes are oxidatively converted to oxy-esters at high selectivity using catalytic amounts of a Group VIII noble metal. If so desired, the alkyl oxy-esters may be converted to alcohols or other intermediates such as alkyl halides. The oxy-esters, alcohols, and other intermediates may optionally be converted to liquid hydrocarbons such as gasoline.

36 Claims, No Drawings

OTHER PUBLICATIONS

I. P. Stolyarov, M. N. Vargaftikh, and I. I. Moiseev, "Selective Oxidation of Methane by Co (III) Trifluorozcetate", Kinetica i Kataliz 1989, 30, 1513–1514 (as translated 1990 Plenum Publishing Corp).

K. G. Ione, V. G. Stepanov, V. N. Romannikov, and S. E. Shepelev, "Synthesis of Hydrocarbons from Compounds Containing One Carbon Atom Using Bifunctional Zeolite Catalysts", Khimiya Teverdogo Topliva 1982, 16, 35–50 (as translated 1982 Atherton Press, Inc.).

V. N. Romannikov and K. G. Ione, "Hydrocarbon Synthesis from $C_1$ Compounds Using Zeolite Catalysts; II. Synthesis for Methyl Chloride", Kinetika i Kataliz 1984, 25, 92–98 (as translated 1984 Plenum Publishing Corporation).

Roger Hunter and Graham J. Hitchings, "Hydrocarbon Formation from Methylating Agents over the Zeolite Catalysts H–ZSM–5 and its Conjugate Base: Evidence against the Trimethyloxonium Ion–Ylide Mechanism", Journal of Chemical Society, Chemical Communications 1985, 1643–1645.

E. S. Rudakov, V. V. Zamshchikov, A. I. Lutsyk, and G. P. Zimtseva, "A New Case of Homogeneous Oxidation of Saturated Hydrocarbons by Platninum Complexes", Zhurnal Fizicheskoi Khimii 1975, 49, 2729–2730 (as translated Russian Journal of Physical Chemistry, 49 (10), 1975).

E. S. Rudakov, V. V. Zamashchikov, A. I. Lutsky, and A. P. Yaroshenko, "Oxidation Kinetics of Saturated Hydrocarbons in the Pd(II)–$H_2SO_4$ and $NO_2^+$–$H_2SO_4$ Systems, Similarity in the Rate–Determining Steps of the Two Reactions", Doklady Akademii Nauk SSSR 1975, 224, 153–156 (as translated 1976 Plenum Publishing Corporation).

V. P. Tret'yakov, E. S. Rudakov, A. A. Galenin, and A. N. Qsetskii "Ruthenium(IV) Complexes: Homogeneous and Heterogeneous Catalysts for the Oxidation of Unsaturated Hydrocarbons", Doklady Akademii Nauk SSSR 1979, 245, 1135–1138 (as translated 1979 Plenum Publishing Corporation).

E. S. Rudakov and R. I. Rudakova, "Palladium Sulfate in Sulfuric Acid—A New Dehydrogenation Reagent Oxidative Dehydrogenation of Cyclohexane to Benzene and of Cycloheptane to the Tropylium Cation", Doklady Akademii Nauk SSSR 1974, 218, 1377–1380 (as translated 1975 Plenum Publishing Corporation).

N. F. Gol'dshleger, M. L. Khidekel', A. E. Shilov, and A. A. Shteinman, "Oxidative Dehydrogenation of Saturated Hydrocarbons in Solutions of PD(II) Complexes", Kinetika i Kataliz 1974, 15, 261 (as Translated 1974 Consultants Bureau, a division of Plenum Publishing Corporation).

PROCESS FOR CONVERTING LOWER ALKANES TO ESTERS

FIELD OF THE INVENTION

This invention is a process for converting lower alkanes into their corresponding esters and optionally into various intermediates (such as methanol) and other liquid hydrocarbons. The alkanes are oxidatively converted to oxy-esters at high selectivity using catalytic amounts of a Group VIII noble metal. If so desired, the alkyl oxy-esters may be converted to alcohols or other intermediates such as alkyl halides. The oxy-esters, alcohols, and other intermediates may optionally be converted to liquid hydrocarbons such as gasoline.

BACKGROUND OF THE INVENTION

The countries of North America currently import significant portions of their needed liquid hydrocarbons from Asia and Africa. Natural gas is abundant on the North American continent but is often present in remote locations. Although natural gas may be liquified and transported for subsequent use, appropriate compression equipment and transportation are quite expensive. Additionally, there are few economically viable technologies available for converting gaseous hydrocarbons to higher molecular weight liquid form materials. This invention includes a highly effective catalytic step useful in converting methane and other lower alkanes to another, more reactive form which may then be converted to normally liquid hydrocarbons.

It is generally accepted that conversion of methane into a reactive intermediate is the most difficult step in the overall conversion of methane into higher molecular weight hydrocarbons (see, for instance, A. E. Shilov and A. A. Shteinman, "Activation of Saturated Hydrocarbons by Metal Complexes in Solutions", *Kinetika i Kataliz*, Vol. 18, No. 5, pp. 1129-1145, 1977).

Several documents disclose a variety of methods for activating methane to produce other higher molecular weight materials.

Mobil Oil Corporation is assignee in several U.S. patents using sulfur or certain sulfur-containing compounds as the reactants in non-catalytic reactions with methane to produce methyl intermediates which can then be converted to higher molecular weight hydrocarbons.

In U.S. Pat. No. 4,543,434 Chang teaches a process using the following steps:

$CH_4 + 4S \longrightarrow CS_2 + 2H_2S$

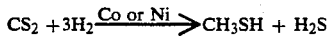
$CS_2 + 3H_2 \xrightarrow{\text{Co or Ni}} CH_3SH + H_2S$

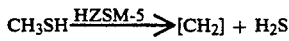
$CH_3SH \xrightarrow{\text{HZSM-5}} [CH_2] + H_2S$

$4H_2S \longrightarrow 4H_2 + 4S$ where "[CH$_2$]" is a hydrocarbon having at least two carbon atoms.

Another Mobil disclosure (U.S. Pat. No. 4,864,073 to Han et al.) suggests a carbonyl sulfide-based process in which methane and carbonyl sulfide are contacted in the presence of ultraviolet light under conditions sufficient to produce CH$_3$SH. No other reaction initiators are said to be present. The reaction scheme is shown to be:

$CH_4 + COS \longrightarrow CH_3SH + CO$

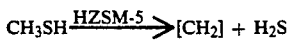
$CH_3SH \xrightarrow{\text{HZSM-5}} [CH_2] + H_2S$

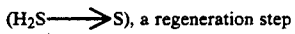
$(H_2S \longrightarrow S)$, a regeneration step

$CO + S \longrightarrow COS$

The selectivity of the first reaction is said to be high, i.e., around 81%; however, the conversion appears to be quite low.

A disclosure similar to that in Chang is found in Mobil's U.S. Pat. No. 4,864,074 to Han et al. As in Chang, the methane is contacted with sulfur. The process conditions are changed, however, so that either CS$_2$ or CH$_3$SH is formed. These sulfur compounds may then be converted in the presence of the preferred HZSM-5 zeolite catalyst to produce hydrocarbons having two or more carbon atoms. Also, as was the case with Chang, the step of contacting the methane to produce a methylsulfur compound is performed in the absence of a catalyst.

Other methods are known for producing substituted methanes which are suitable for further reaction to heavier hydrocarbons. A thermal methane chlorination process is shown in U.S. Pat. No. 4,804,797 to Minet et al. A similar process is disclosed in U.S. Pat. No. 3,979,470 to Firnhaber et al. although a preference for C$_3$ hydrocarbon feeds is expressed.

One method shown in U.S. Pat. No. 4,523,040 to Olah utilizes either a solid strongly acidic catalyst or a supported Group VIII metal (particularly platinum and palladium) in the gas phase halogenation of methane to produce methyl halides. The patent indicates that monohalides are produced in 85% to 99% selectivity. Olah suggests that subsequent or concurrent catalytic hydrolysis produces methyl alcohol and/or dimethyl ether. Production of methyl oxy-esters is not shown.

The reaction of methane with palladium (II) acetate in trifluoroacetic acid to effect the trifluoroacetoxylation of methane is shown in Sen et al., "Palladium (II) Mediated Oxidative Functionalization of Alkanes and Arenes", *New Journal of Chemistry* (1989), Vol. 13, No. 10-11, pp. 756-760. A yield of 60% based on palladium was reported when the process was practiced using methane as the reactant. Consequently, the reaction utilized palladium as a reactant and not as a catalyst. Palladium was shown in the article to be catalytic in the trifluoroacetoxylation of an arene.

The Sen et al. article has been criticized in Vargaftik et al., "Highly Selective Partial Oxidation of Methane to Methyl Trifluoroacetate", *Journal of the Chemical Society, Chemical Communications* (1990), pp. 1049-1050, to the extent that the results were not found to be reproducible. Vargaftik et al. discloses the catalytic oxy-esterification of methane with cobalt but shows that palladium is not even suitable for stoichiometric methane oxidation in that process. Less than 0.1% yield of methyl trifluoroacetate based on palladium (II) trifluoroacetate was obtained.

Our inventive process is the first of which we are aware in which a lower alkane is oxidized to a an oxy-ester intermediate using a Group VIII noble metal catalyst, which intermediate is suitable for further conversion into heavier liquid hydrocarbons.

SUMMARY OF THE INVENTION

This invention is a catalytic oxidation process for the conversion of lower alkanes into alkyl oxy-esters which may ultimately be converted into hydrocarbons (desirably in the gasoline boiling range) or alcohols.

The first step is catalytic and involves the contacting of a lower alkane (such as methane) with an acid, a catalyst comprising a Group VIII noble metal, and an oxidizing agent. The reaction may take place at low pressures and temperatures. The preferred Group VIII metal catalyst is palladium and the preferred oxidizing agent is oxygen. The alkane is converted to an alkyl oxy-ester of the acid which is relatively inert to further oxidation under the reaction conditions.

The esters produced in the first step may then be converted to alcohols or to other suitable intermediates. This step may be used to regenerate the acid for recycle and reuse in the first step.

The alcohols or other intermediates may then be converted to higher hydrocarbons, preferably suitable for direct use as a fuel but at least suitable for further processing to higher hydrocarbons or chemicals. The alcohols can be used directly as a fuel.

DESCRIPTION OF THE INVENTION

As noted above, this invention includes both the overall process for producing higher hydrocarbons and the individual step of esterifying lower alkanes such as methane.

The overall process, using methane as an example, may be outlined in the following fashion:

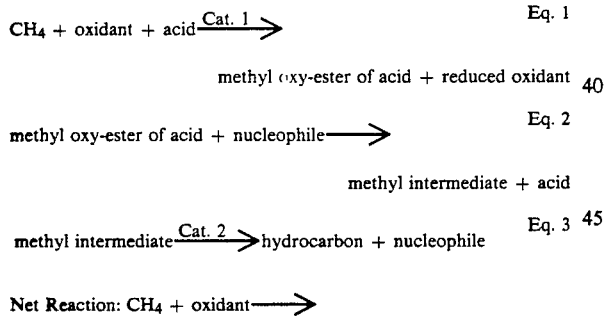

FIRST STEP

The first step (utilizing the reaction of Eq. 1) involves contacting methane with an acid and an oxidizing agent in the presence of a catalyst. The acid HX (where X is the acid's anion) may be an organic or inorganic acid such as $HNO_3$, $H_2SO_4$, $CF_3CO_2H$, $CF_3SO_3H$, $H_3PO_4$, or the like. The preferred acids are strong inorganic acids (pKa<2.0) and especially preferred are $H_2SO_4$ and $CF_3SO_3H$. The acids should be oxidation resistant: they should not be oxidized by the catalyst metal in the noted reaction medium. In addition to acting as a reactant, the acid desirably is used in excess and thereby acts as a reaction medium as well.

The oxidizing agent generally may be a strong oxidant, e.g., a halogen (such as $Cl_2$), $HNO_3$, perchloric acid, hypochlorites (such as NaOCl), $O_2$ or $O_3$, $SO_3$, $NO_2$, $H_2O_2$, $H_2SO_4$, etc. Some selection of oxidizing agent is necessary. For instance, halogens may work with platinum but we have found that they work poorly (if at all) with palladium. Oxygen is preferred because of its ready availability. Where $O_2$ is the oxidant, the manner of accomplishing Eq. 1 is as follows:

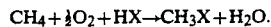

Where $H_2SO_4$ is both the oxidant and the acid, the process for accomplishing Eq. 1 is as follows:

$$CH_4 + 2H_2SO_4 \rightarrow CH_3OSO_3H + 2H_2O + SO_2.$$

Where $SO_3$ is the oxidant and $H_2SO_4$ is the acid, the process for accomplishing the reaction of Eq. 1 is as follows:

Where $O_2$ is the oxidant and $CF_3SO_3H$ is the acid, the process for accomplishing the reaction of Eq. 1 is as follows:

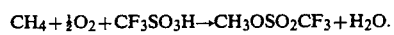

The catalyst used in Eq. 1 is one or more Mendelev transition metals which will cause the oxidation of hydrogen, alkanes, or arenes. For a discussion of such an oxidation, see Olah et al., "Superacid-Catalyzed Oxygenation of Alkanes", *Angew. Chem., Int. Ed.*, (1978) Vol. 17, pp. 909-931. Preferred catalysts include metals selected from the Group VIII noble metals, i.e., platinum, palladium, iridium, ruthenium, rhodium, osmium, and mixtures of those metals. The preferred catalyst is palladium but one or more of the noted metals may be used as the catalytic material. The form in which the catalyst is introduced to the reaction is not particularly important; the requirements being only that it be in a form allowing oxidant, acid, and reactant access to the metal and that the form not restrict the ability of the catalytic metal to vary between oxidation states during the reaction. For instance, when palladium is introduced as a metal, salt, or complex into a liquid reaction medium, palladium varies between the +2 state and the 0 state during the reaction. The palladium is likely soluble in the +2 state but perhaps is not soluble (or forms micron-size solids) during its sojourn into the 0 state. The catalytic metal (or metals) may be placed on the usual catalyst supports provided the supports do not interfere with the requirements listed above. We have found that introducing the metal to the liquid reaction medium in a form which produces a homogeneous catalyst is very desirable. The metal may be introduced to the liquid reaction medium in a convenient form such as the salt of the acid used in Eq. 1, although that is not required. The metallic form of the catalyst may also be used. The catalyst metal concentration must be present in at least a catalytic amount; amounts of metal ranging between 50 ppm and 1.0% by mole of the total liquid present are effective. We have also found that the catalyst is more efficient at lower concentrations.

The process or esterification conditions used in the first step are as follows:

a. temperature is greater than 50° C., preferably 50° C. to 250° C., and most preferably 95° C. to 200° C.;

b. methane is added at a pressure above about 50 psig, preferably above about 300 psig, and most preferably above about 450 psig; and c. oxidant (whether pure or with other inert diluents) is added in an amount sufficient to support the reaction. These conditions result in production of the alkyl oxy-ester of the acid in a molar amount greater than the molar amount of the catalyst metal charged in the reactor therefore giving a truly catalytic process.

Use of devices for promoting good mixing between the gas and liquid phases is desirable.

SECOND STEP

This step is shown above as Eq. 2. It is an optional step and is carried out generally for the purpose of replacing the oxy-ester formed in the first step with an intermediate which is both reactive in the third step and does not substantially degrade the catalyst used in that later step.

The methyl ester should be separated from the first step reaction media by commonly practiced steps such as flashing or distillation. The nucleophile in Eq. 2 is suitably then mixed with the methyl oxy-ester to produce a "methyl intermediate". By "methyl intermediate" is meant methanol, if the nucleophile is $H_2O$; methyl halide, if the nucleophile is a hydrogen halide such as HCl, HBr, or HI; methyl amino, if the nucleophile is $NH_3$; or a methyl thiol, if the nucleophile is $H_2S$. These reactions proceed readily to completion. An excess of the nucleophile is desirable. The preferred nucleophile is $H_2O$ since it may also be produced in the first step. The product methanol may be used directly or may be converted to a variety of hydrocarbons in a following step or steps.

THIRD STEP

This step (shown above as Eq. 3) includes conversion of the methyl intermediate to a longer chain or higher molecular weight hydrocarbon.

Suitable processes for converting methanol and other methyl intermediates to higher molecular weight hydrocarbons are found in U.S. Pat. Nos. 3,894,107 and 3,979,472 to Butter et al. Butter shows the production of olefinic and aromatic compounds by contacting the methyl intermediate with an aluminosilicate catalyst, preferably HZSM-5, at a temperature between 650° F. and 1000° F.

Similarly, Butter suggests a process using a preferable catalyst of antimony oxide and HZSM-5 at a temperature between 250° C. and 700° C.

The ZSM-5 zeolite has been disclosed as a suitable molecular sieve catalyst for converting methyl alcohol into gasoline-range hydrocarbons. See, for instance, U.S. Pat. Nos. 3,702,886 to Argauer et al. and 3,928,483 to Chang et al.

Other processes include those described in U.S. Pat. No. 4,373,109 to Olah (bifunctional acid-base catalyzed conversion of methanol and other methyl intermediates into lower olefins); U.S. Pat. No. 4,687,875 to Currie et al. (metal coordination complexes of heteropolyacids as catalysts for converting short chain aliphatic alcohols to short change hydrocarbons); U.S. Pat. No. 4,524,234 to Kaiser (production of hydrocarbons preferably from methanol using aluminophosphate molecular sieves); and U.S. Pat. No. 4,579,996 to Font Freide et al. (production of hydrocarbons from $C_1$ to $C_4$ monohaloalkanes using layered clays); etc. Each of the above is potentially suitable for the third step of this process and their contents are incorporated by notice.

INTEGRATED PROCESS

Where the process steps outlined as Eqs. 1-3 above are integrated, as might be done in an operating plant, $O_2$ is the oxidant and HY is a nucleophile, the overall process scheme is as follows:

$$CH_4 + \tfrac{1}{2}O_2 + HX \longrightarrow CH_3X + H_2O$$

$$CH_3X + HY \longrightarrow CH_3Y + HX$$

$$CH_3Y \longrightarrow [CH_2] + HY$$

Net Reaction: $CH_4 + \tfrac{1}{2}O_2 \longrightarrow [CH_2] + H_2O$

Where $H_2SO_4$ is both the oxidant and the acid and water is the nucleophile, the process for accomplishing the overall process is as follows:

$$CH_4 + 2\,H_2SO_4 \longrightarrow CH_3OSO_3H + 2\,H_2O + SO_2$$

$$SO_2 + \tfrac{1}{2}O_2 + H_2O \longrightarrow H_2SO_4$$

$$CH_3OSO_3H + H_2O \longrightarrow CH_3OH + H_2SO_4$$

$$CH_3OH \longrightarrow [CH_2] + H_2O$$

$$CH_2 + \tfrac{1}{2}O_2 \longrightarrow [CH_2] + H_2O$$

It should be understood that the first two reactions expressed immediately above are equivalent in sum to Eq. 1 of the overall process.

Where $SO_3$ is the oxidant, $H_2SO_4$ is the acid, and water is the nucleophile, the process for accomplishing the overall process is as follows:

$$CH_4 + SO_3 + H_2SO_4 \longrightarrow CH_3OSO_3H + SO_2$$

$$SO_2 + \tfrac{1}{2}O_2 \longrightarrow SO_3$$

$$CH_3OSO_3H + H_2O \longrightarrow CH_3OH + H_2SO_4$$

$$CH_3OH \longrightarrow [CH_2] + H_2O$$

Net Reaction: $CH_4 + \tfrac{1}{2}O_2 \longrightarrow [CH_2] + H_2O$

It should be understood that the first two reactions expressed immediately above are equivalent in sum to Eq. 1 of the overall process.

Where $O_2$ is the oxident, $CF_3SO_3H$ is the acid, and water is the nucleophile, the process is as follows:

$$CH_4 + \tfrac{1}{2}O_2 + CF_3SO_3H \longrightarrow CH_3OSO_2CF_3 + H_2O$$

$$CH_3OSO_2CF_3 + H_2O \longrightarrow CH_3OH + CF_3SO_3H$$

-continued

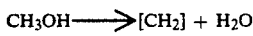

Net Reaction: 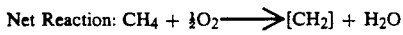

These reaction schemes permit regeneration and recycle of the acid and, in some instances, the auxiliary oxidant, which makes the process more economical. Some acids require additional steps to separate the neucleophile but such steps are known to the ordinarily skilled worker.

EXAMPLES

These examples are intended to show portions of the overall inventive process, in particular the alkyl esterification reaction utilizing methane as the reactant. The remainder of the process steps are easily selectable from known processes.

EXAMPLE 1

This example shows the use of a palladium catalyst, $SO_3$ as oxidant, and $H_2SO_4$ as the acid in esterifying methane.

A 100 ml glass reactor having an integral heater-stirrer was loaded with 15 ml of oleum (20% $SO_3$) and 0.0304 gm $PdSO_4 \cdot 2H_2O$ ($1.27 \times 10^{-4}$ mol). The system was purged with $N_2$ and pressured to 100 psig with $CH_4$. The stirrer and heater were started. During heat-up, the pressure was adjusted to maintain about 100 psig. The reaction was carried out at about 100° C. and 100 psig. After about three hours, the reactor was cooled to about 25° C., the pressure bled down, and samples of the gaseous effluent taken. Samples of the reactor solution (in range of color from orange to red without black precipitate) were also taken.

The gases in the reactor were analyzed using a gas chromatograph and the gas remaining in the reactor contained $CH_4$, $2.96 \times 10^{-4}$ mols carbon dioxide and $9.28 \times 10^{-3}$ mols $SO_2$.

The reaction produced a large amount of $SO_2$ caused by the reoxidation of $Pd^0$. The yield of the methyl ester $CH_3OSO_3H$ was $3.6 \times 10^{-3}$ mols as determined by saponification of the reaction samples and subsequent analysis of the released $CH_3OH$. This shows a 2834% yield on palladium and verifies that palladium is catalytic in the process. The yield of methyl ester was also confirmed by H-NMR (using internal standards in coaxial tubes).

EXAMPLE 2

This example demonstrates the use of $H_2SO_4$ both as an oxidant and as esterfying acid in the reaction.

The process of Example 1 was repeated except that $SO_3$ was omitted. An amount of 8.5 ml of $H_2SO_4$ was used both as the acid and oxidant. The $PdSO_4 \cdot 2H_2O$ was added in an amount of 0.0035 gm ($1.5 \times 10^{-5}$ mol).

The gas chromatograph data showed $6.64 \times 10^{-4}$ mols of $SO_2$ in the reactor along with $2.85 \times 10^{-4}$ mols carbon dioxide. The yield of $CH_3OSO_3H$ was $1.46 \times 10^{-4}$ mols or a 970% yield on the amount of palladium present in the reactor. The reaction was catalytic in the palladium metal.

EXAMPLE 3

This example shows the use of $O_2$ as the oxidant, $H_2SO_4$ as the esterfying acid, and palladium as the catalyst. In addition, the process is a continuous feed operation rather than a batch operation as shown in Examples 1 and 2.

A 150 ml TEFLON-lined reactor having an integral heater-stirrer was loaded with 20 ml of $H_2SO_4$ and 0.478 gm ($2 \times 10^{-3}$ mol) $PdSO_4 \cdot 2H_2O$. The system was purged with $N_2$ and pressured to 600 psig with $CH_4$. The stirrer and heater were started. The reaction was carried out at 175° C. The effluent gas was continuously sampled. The feed gases were introduced at 20 cc/minute of $O_2$ ($8.9 \times 10^{-4}$ mol/minute) and 80 cc/minute of $CH_4$ ($3.6 \times 10^{-3}$ mol/minute).

At about two hours, the molar ratio of $CH_4/O_2$ stabilized at about 4/1 and the system pressure stabilized at 625 psig. After about six hours the reaction was terminated by cooling the reactor to 50° C.

Gas chromatograph analysis of the gases showed that, on the average, $7.59 \times 10^{-3}$ mols of carbon dioxide and $9.28 \times 10^{-4}$ mols of $SO_2$ were produced. The yield of $CH_3OSO_3H$ was $5.0 \times 10^{-3}$ mols for a yield of 250% based on the amount of palladium present.

Again, this demonstrates the palladium metal to be catalytic in this process.

EXAMPLE 4

This example shows the catalytic esterification of methane using $CF_3SO_3H$ (triflic acid) as the acid, $O_2$ as the oxidant, and palladium as the catalyst.

A 50 ml Hastalloy C reactor equipped with a stirrer was loaded with 30 ml of triflic acid, 0.2 ml $H_2O$, and 0.25 g of palladium black ($Pd^0$). The reactor was pressured to 500 psig with pure $O_2$, heated to 180° C., and stirred for two hours to convert the palladium black to the catalytically active form.

The reactor was cooled and purged with $N_2$ to remove the $O_2$. The reactor was pressured to 1000 psig with $CH_4$. A flow of 200 standard cc/minute of $CH_4$ was then established. The gas leaving the reactor was scrubbed using aqueous $Na_2CO_3$. A flow of 50 standard cc/minute of $O_2$ was then introduced, the reactor heated to 180° C., and stirring commenced. The exiting gases were periodically analyzed for carbon dioxide and other product gases.

The reaction was terminated at three hours by stopping the gas flows and allowing the reactor to cool to room temperature. The reactor head space was vented through the $Na_2CO_3$ trap. The contents of the reactor, $Na_2CO_3$ trap, and the exit gases were analyzed for methyl triflate, methanol, carbon dioxide, and other products.

The only carbon-containing products were methanol, methyl triflate, and carbon dioxide. Less than 5% of the methane consumed was converted to carbon dioxide. The sum of the amounts of methyl ester (methyl triflate) found in the reactor and methanol found in the $Na_2CO_3$ trap (due to in situ saponification) was calculated to produce a yield of 500% based on palladium.

EXAMPLE 5

This is a comparative example which shows the need for an oxidant in the process in order to obtain catalysis with respect to palladium. Specifically, methane was used as the lower alkane, $CF_3SO_3H$ (triflic acid) as the acid, and palladium as the oxidant.

A 50 ml Hastalloy C reactor equipped with a stirrer was loaded with 30 ml of triflic acid ($CF_3SO_3H$), 0.2 ml $H_2O$, and 0.25 g of palladium black ($Pd^0$). The reactor was pressured to 500 psig with pure $O_2$, heated to 180°

C., and stirred for two hours to convert the palladium black to the oxidant.

The reactor was cooled and purged with $N_2$ to remove the $O_2$. The reactor was pressured to 600 psig with $CH_4$. In Example 4, 50 cc/minute of $O_2$ was introduced into the reactor; oxygen was not included in this example. The reactor was heated to 180° C., the pressure adjusted to 1000 psig with $CH_4$ and stirring commenced.

The reaction was terminated at three hours by allowing the reactor to cool to room temperature. The reactor head space was vented through a $Na_2CO_3$ trap. The contents of the reactor, $Na_2CO_3$ trap, and the exit gases were analyzed for methyl triflate, methanol, carbon dioxide, and other products.

The only carbon-containing products were methanol, methyl triflate, and carbon dioxide. Only trace amounts of carbon dioxide were detected. The sum of the amounts of methyl ester (methyl triflate) found in the reactor and methanol found in the $Na_2CO_3$ trap (due to in situ saponification) provided a yield of 92% based on palladium. Without the added oxidant (such as $O_2$ as used in Example 4) the palladium was not catalytic.

The invention has been shown both by description and by example. The examples are only examples; they should not be used in any fashion to limit the scope of the invention otherwise described here.

Additionally, it should be clear that one having ordinary skill in this art would envision equivalents to the processes described in the claims that follow and these equivalents would be within the scope and spirit of the claimed invention.

We claim as our invention:

1. A process for converting one or more lower alkanes to higher molecular weight hydrocarbons comprising the steps of:
   a. contacting one or more lower alkanes, an oxidizing agent, a strong mineral acid, and a catalyst comprising a Group VIII noble metal at esterification conditions to produce a lower alkyl oxy-ester of the acid in a molar amount greater than the molar amount of Group VIII noble metal,
   b. converting the lower alkyl oxy-ester of the acid to an alkyl intermediate, and
   c. catalytically converting the alkyl intermediate to higher molecular weight hydrocarbons.

2. The process of claim 1 where the lower alkane comprises methane.

3. The process of claim 2 where the alkyl intermediate comprises methanol.

4. The process of claim 2 where the oxidizing agent is selected from halogens, $HNO_3$, perchloric acid, HOCl, $O_2$, $O_3$, $SO_3$, $NO_2$, $H_2O_2$, and $H_2SO_4$.

5. The process of claim 4 where the oxidizing agent is $O_2$.

6. The process of claim 4 where the oxidizing agent is $SO_3$.

7. The process of claim 4 where the oxidizing agent is $H_2SO_4$.

8. The process of claim 2 where the acid is selected from $HNO_3$, $H_3PO_4$, $H_2SO_4$, $CF_3SO_3H$, and $CF_3CO_2H$.

9. The process of claim 8 where the acid is $H_2SO_4$.

10. The process of claim 8 where the acid is $CF_3SO_3H$.

11. The process of claim 5 where the acid is $CF_3SO_3H$.

12. The process of claim 2 where the Group VIII noble metal is palladium or platinum.

13. The process of claim 10 where the Group VIII noble metal is palladium.

14. The process of claim 11 where the Group VIII noble metal is palladium.

15. The process of claim 4 where the Group VIII noble metal is palladium.

16. The process of claim 5 where the Group VIII noble metal is palladium.

17. The process of claim 9 where the Group VIII noble metal is palladium.

18. The process of claim 4 where the methyl intermediate is methanol.

19. The process of claim 5 where the methyl intermediate is methanol.

20. The process of claim 9 where the methyl intermediate is methanol.

21. The process of claim 10 where the methyl intermediate is methanol.

22. The process of claim 18 where methanol is converted to higher molecular weight hydrocarbons using a HZSM-5 catalyst.

23. A process for esterifying one or more lower alkanes comprising the steps of:
   a. contacting the one or more lower alkanes, an oxidizing agent, a strong mineral acid, and a catalyst comprising a Group VIII noble metal at esterification conditions to produce a lower alkyl oxy-ester of the acid in a molar amount greater than the molar amount of the Group VIII metal, and
   b. recovering the lower alkyl oxy-ester of the acid.

24. The process of claim 23 where the lower alkane comprises methane.

25. The process of claim 24 where the oxidizing agent is selected from halogens, $HNO_3$, perchloric acid, HOCl, $O_2$, $O_3$, $SO_3$, $NO_2$, $H_2O_2$, and $H_2SO_4$.

26. The process of claim 25 where the oxidizing agent is $O_2$.

27. The process of claim 25 where the oxidizing agent is $SO_3$.

28. The process of claim 25 where the oxidizing agent is $H_2SO_4$.

29. The process of claim 25 where the acid is selected from $HNO_3$, $H_3PO_4$, $H_2SO_4$, $CF_3SO_3H$, and $CF_3CO_2H$.

30. The process of claim 29 where the acid is $H_2SO_4$.

31. The process of claim 29 where the acid is $CF_3SO_3H$.

32. The process of claim 26 where the acid is $CF_3SO_3H$.

33. The process of claim 25 where the Group VIII noble metal is palladium or platinum.

34. The process of claim 29 where the Group VIII noble metal is palladium.

35. The process of claim 32 where the Group VIII noble metal is palladium.

36. The process of claim 33 where the Group VIII noble metal is palladium.

* * * * *